United States Patent [19]

Pelosi, Jr.

[11] Patent Number: 5,091,426
[45] Date of Patent: Feb. 25, 1992

[54] 5-PHENYL-2-FURAN KETONES AND USE AS ANTIEPILEPTIC AGENTS

[75] Inventor: Stanford S. Pelosi, Jr., Norwich, N.Y.

[73] Assignee: Norwich Eaton Pharmaceuticals, Inc., Norwich, N.Y.

[21] Appl. No.: 371,354

[22] Filed: Jun. 23, 1989

[51] Int. Cl.$^5$ .................... B61K 31/34; C07D 307/46
[52] U.S. Cl. .................... 514/231.5; 514/252;
514/326; 514/374; 514/422; 514/461; 514/471;
544/152; 544/379; 546/214; 548/215; 548/517;
549/483; 549/488
[58] Field of Search .............. 549/483, 488; 548/215,
548/517; 546/214; 544/192, 379; 514/231.5,
292, 326, 374, 472, 461, 471

[56] References Cited

U.S. PATENT DOCUMENTS

| | | | |
|---|---|---|---|
| 3,856,825 | 12/1974 | Wright et al. | 260/347.5 |
| 4,031,113 | 6/1977 | Pelosi | 549/488 X |
| 4,035,394 | 7/1977 | Pelosi et al. | 549/488 |
| 4,085,118 | 4/1978 | Pelosi | 549/488 X |

OTHER PUBLICATIONS

Oleinik, A. F. et al., "Amino- and Hydroxaminoderivatives of Arylfurans", *Khimia Geterotsiklicheskikh Soedinentii* 11:1448-1452, 1972.

Goldenberg, M., "F-461, 3-diethylamino-2,2-dimethylpropyl 5-(P-nitrophenyl)-2-furoate hydrochloride, a new non-anticholinergic spasmolytic and a gastric acid inhibitor", *Arch. Int. Pharmacodyn*, vol. 222, pp. 27-39 (1976).

Oleinik, A. F. et al., "Synthesis and Tuberculostatic Activity of 5-arylpyromucic acid derivatives", *Pharmaceutical Chemical Journal*, vol. 10, No. 4 (Apr. 1976), pp. 463-465.

Olenik et al, C.A. vol 78 (1973), 43109q.

*Primary Examiner*—Richard L. Raymond
*Attorney, Agent, or Firm*—David L. Suter; Karen F. Clark; Jack D. Schaeffer

[57] ABSTRACT

A method of preventing epileptic seizures in a human or lower animal subject susceptible to said seizures, comprising systemically administering to said subject a safe and effective amount of a compound of the formula:

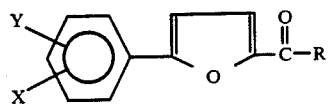

wherein
(a) X is halo or nil, and Y is a substituent selected from the group consisting of unsubstituted or halogen-substituted methyl, halo, nitro, amino, and methoxy; and
(b) R is R$^1$C(O)OH, R$^1$C(O)N(R$^2$)$_2$, or R$^1$N(R$^2$)$_2$;
where
R$^1$ is C$_1$-C$_3$ alkylene which is unsubstituted or substituted with C$_1$-C$_2$ alkyl; and
each R$^2$ is, independently, hydrogen or lower alkyl; or
both R$^2$ groups are connected to form a saturated 5- or 6-membered heterocycle containing 1 or 2 heteroatoms, wherein one of which is nitrogen and the other is selected from oxygen and nitrogen and said heterocycle is unsubstituted or substituted with lower alkyl or hydroxy-substituted lower alkyl;

or a pharmaceutically-acceptable salt thereof. Preferably X is halo.

21 Claims, No Drawings

5-PHENYL-2-FURAN KETONES AND USE AS ANTIEPILEPTIC AGENTS

BACKGROUND OF THE INVENTION

This invention relates to certain novel 5-phenyl-2-furan ketones useful as antiepileptic agents.

Antiepileptic agents are used to treat seizure disorders. Approximately 2.5 million of all Americans have epilepsy. Epilepsy often begins in childhood, with three quarters of the patients having their first seizure before the age of 18. Two hundred thousand Americans have epileptic seizures more than once a month. Most epileptic patients are dependent on drugs to control seizures, but therapy is often inadequate. For certain types of seizures there are no specific drugs available.

The modern history of antiepileptic drugs marketed in the United States began in 1912 with the introduction of phenobarbital, a synthetic sedative-hypnotic drug which was shown to reduce seizure frequency. Since the barbituric acid molecule is easily modified, many analogs of phenobarbital were synthesized and marketed for antiepileptic activity. Antiepileptic drug development then entered a dormant period lasting for twelve years, from 1961 to 1973, during which the only new drug of interest was diazepam, an adjunctive drug used mostly in status epilepticus.

In 1968, the Epilepsy Branch of the National Institute of Neurological and Communicative Disorders attempted to reverse the decline in antiepileptic drug development by conducting controlled clinical trials of several drugs that needed proof of efficacy. The resulting data eventually supported new drug applications for carbamazepine in 1974, clonazepam in 1975 and valproic acid in 1978.

Many patients with common types of seizures and most of those with rare types fail to respond to available drugs and/or suffer adverse side effects. The currently available antiepileptic drugs have many adverse side effects. They include cardiovascular collapse, central nervous system depression, aplastic anemia, congestive heart failure, visual hallucinations, liver damage, cognitive impairment, ataxia, personality changes, psychosis, aggressive behavior, nausea, dizziness and sedative effects. For those patients whose seizures are controlled with currently available therapy, a new drug may allow a reduction in the adverse side effects. It has been discovered that certain 5-phenyl-2-furan ketones have antiepileptic activity, these compounds are potentially less toxic and/or have greater efficacy than current agents used clinically as antiepileptic agents.

A number of 5-phenyl-2-furan esters and amides are described in the literature. However, these compounds have never been suggested to have antiepileptic activity. For example, U.S. Pat. No. 3,856,825 issued to Wright et al. on Dec. 24, 1974, discloses a series of 3-diethylamino-2,2-dimethylpropyl 5-(substituted phenyl)-2-furoates that possess pharmacological properties, particularly being useful as antispasmodics. U.S. Pat. No. 4,162,257 issued to Pelosi and Yu on July 24, 1979, discloses N,N-dimethyl-5-phenyl-2-furamides said to be useful as anti-inflammatory agents. Oleinik, A. F. et al., "Synthesis and Tuberculostatic Activity of 5-Arylpyromucic Acid Derivatives", *Pharmaceutical Chemical Journal*. Vol. 10, No. 4 (April, 1976), pages 463–465, discloses certain 5-phenyl-2-furans said to have bacteriostatic activity.

SUMMARY OF THE INVENTION

The present invention encompasses certain 5-phenyl-2-furan ketones and compositions thereof. It also encompasses methods of using these compounds to prevent epileptic seizures in a human or lower animal subject susceptible to such seizures. Specifically, the compounds of this invention are of the formula:

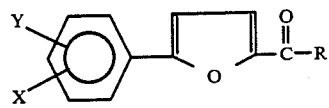

wherein
(1) X is halo or nil; and Y is a substituent selected from the group consisting of unsubstituted or halogen-substituted methyl, halo, nitro, amino, and methoxy; and
(2) R is $R^1C(O)OH$, $R^1C(O)N(R^2)_2$, or $R^1N(R^2)_2$; where
$R^1$ is $C_1$–$C_3$ alkylene which is unsubstituted or substituted with $C_1$–$C_2$ alkyl; and
each $R^2$ is, independently, hydrogen or lower alkyl; or
both $R^2$ groups are connected to form a saturated 5- or 6-membered heterocycle containing 1 or 2 heteroatoms, wherein one of which is nitrogen and the other is selected from oxygen and nitrogen, and said heterocycle is unsubstituted or substituted with lower alkyl or hydroxy-substituted lower alkyl;

or a pharmaceutically-acceptable salt thereof.

DESCRIPTION OF THE INVENTION

The present invention encompasses certain 5-phenyl-2-furan ketones and compositions (hereinafter referred to as "5-phenyl furans"). It also encompasses methods for using these compounds to prevent epileptic seizures in a human or other animal susceptible to such seizures. Specific compounds and compositions to be used in the invention must, accordingly, be pharmaceutically acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio.

COMPOUNDS

The present invention provides novel 5-phenyl furans of the chemical structure:

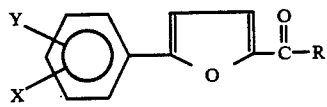

wherein
(1) X is halo or nil; and Y is a substituent selected from the group consisting of unsubstituted or halogen-substituted methyl, halo, nitro, amino, and methoxy; and
(2) R is $R^1C(O)OH$, $R^1C(O)N(R^2)_2$, or $R^1N(R^2)_2$; where
$R^1$ is $C_1$–$C_3$ alkylene which is unsubstituted or substituted with $C_1$–$C_2$ alkyl; and each $R^2$ is, independently, hydrogen or lower alkyl; or both $R^2$ groups are connected to form a saturated 5- or 6-membered heterocycle containing 1 or 2 heteroatoms wherein one of which is nitrogen and the other is selected from oxygen and nitrogen, ad said heterocycle is unsubstituted or substituted with lower alkyl or hydroxy-substituted lower alkyl;

or a pharmaceutically-acceptable salt thereof. "Lower alkyl" is a 1 to 6 carbon chain; preferably a 1 to 3 carbon chain.

Preferred 5-phenyl furans include those compounds wherein X is a meta or para substituent and is selected from the group consisting of fluoro, chloro, and bromo. Preferred 5-phenyl furans also include those wherein Y is selected from the group consisting of halogen substituted methyl, fluoro, chloro, bromo and methoxy. A particularly preferred 5-phenyl furan is one wherein Y is trifluoromethyl. Preferred compounds useful in the methods of this invention include:

3dimethylamino-1-[5-(4-fluorophenyl)-2-furanyl]-1-propanone hydrochloride;
3-dimethylamino-1-[5-(4-bromophenyl)-2-furanyl]-1-propanone hydrochloride;
3-dimethylamino-1-[5-(3-bromophenyl)-2-furanyl]-I-propanone hydrochloride;
3-dimethylamino-1-5-(4-trifluoromethylphenyl)-2-furanyl]-1-propanone hydrochloride;
3-dimethylamino-1-[5-(3-trifluoromethylphenyl)-2-furanyl]-1-propanone hydrochloride;
3-dimethylamino-1-[5-(3,5-dichlorophenyl)-2-furanyl]-1-propanone hydrochloride;
3-dimethylamino-1-[5-(3,5-difluorophenyl)-2-furanyl]-1-propanone hydrochloride;
3-dimethylamino-1-(5-phenyl-2-furanyl)-1-propanone hydrochloride tetartohydrate;
3-dimethylamino-1-[5-(4-chlorophenyl)-2-furanyl]-1-propanone hydrochloride;
3-dimethylamino-1-[5-(4-methoxyphenyl)-2-furanyl]-1-propanone hydrochloride;
1-[5-(4-chlorophenyl)-2-furanyl]-3-[1-(4-methylpiperazinyl)]-1-propanone dihydrochloride hemihydrate;
1-[5-(2-nitrophenyl)-2-furanyl]-3-(1-piperidinyl)-1-propanone hydrochloride;
3-[5-(4-chlorophenyl)-2-furanyl]-3-oxopropanamide;
1-[5-(4-bromophenyl)-2-furanyl]-3-(1-pyrrolidinyl)-1-propanone;
1-[5-(4-chlorophenyl)-2-furanyl]-3-(1-piperazinyl)-1-propanone;
4-[5-(4-chlorophenyl)-2-furanyl]-4-oxobutanoic acid;
1-[5-(4-chlorophenyl)-2-furanyl]-3-(1-pyrrolidinyl)-1-propanone hydrochloride;
1-[5-(4-chlorophenyl)-2-furanyl]-3-(1-piperidinyl)-1-propanone hydrochloride;
1-[5-(3,4-dichlorophenyl)-2-furanyl]-3-(1-piperidinyl)-1-propanone hydrochloride;
1-[5-(4-fluorophenyl)-2-furanyl]-3-(1-piperidinyl)-1-propanone hydrochloride;
1-[5-(3-chlorophenyl)-2-furanyl]-3-(1-piperidinyl)-1-propanone hydrochloride;
1-[5-(4-bromophenyl)-2-furanyl]-3-(1-piperidinyl)-1-propanone hydrochloride;
1-[5-(4-chlorophenyl)-2-furanyl]-3-[1-(3-methylpiperidinyl)]-1-propanone hydrochloride;
1-[5-(4-chlorophenyl)-2-furanyl]-3-[1-(3-hydroxymethylpiperidinyl)]-1-propanone hydrochloride;
1-[5-(4-chlorophenyl)-2-furanyl]-2-(diethylamino)ethanone hydrochloride;
3-diethylamino-1-[5-(p-chlorophenyl)-2-furyl]-1-propanone hydrochloride.

More preferred 5-phenyl furans include:
3-dimethylamino-1-[5-(4-fluorophenyl)-2-furanyl]-1-propanone hydrochloride;
3-dimethylamino-1-[5-(4-bromophenyl)-2-furanyl]-1-propanone hydrochloride;
3-dimethylamino-1-[5-(3-bromophenyl)-2-furanyl]-1-propanone hydrochloride;
3-dimethylamino-1-[5-(4-trifluoromethylphenyl)-2-furanyl]-1-propanone hydrochloride;
3-dimethylamino-1-[5-(3-trifluoromethylphenyl)-2-furanyl]-1-propanone hydrochloride;
3-dimethylamino-1-[5-(3,5-difluorophenyl)-2-furanyl]-1-propanone hydrochloride;
3-dimethylamino-1-(5-phenyl-2-furanyl)-1-propanone hydrochloride tetartohydrate;
3-dimethylamino-1-[5-(4-chlorophenyl)-2-furanyl]-1-propanone hydrochloride;
3-dimethylamino-1-[5-(4-methoxyphenyl)-2-furanyl]-1-propanone hydrochloride;
1-[5-(4-chlorophenyl)-2-furanyl]-3-[1-(4-methylpiperazinyl)]-1-propanone dihydrochloride hemihydrate;
1-[5-(2-nitrophenyl)-2-furanyl]-3-(1-piperidinyl)-1-propanone hydrochloride;
3-[5-(4-chlorophenyl)-2-furanyl]-3-oxopropanamide;
1-[5-(4-chlorophenyl)-2-furanyl]-3-(1-pyrrolidinyl)-1-propanone hydrochloride;
1-[5-(4-chlorophenyl)-2-furanyl]-3-(1-piperidinyl)-1-propanone hydrochloride;
1-[5-(3,4-dichlorophenyl)-2-furanyl]-3-(1-piperidinyl)-1-propanone hydrochloride;
1-[5-(4-fluorophenyl)-2-furanyl]-3-(1-piperidinyl)-1-propanone hydrochloride;
1-[5-(3-chlorophenyl)-2-furanyl]-3-(1-piperidinyl)-1-propanone hydrochloride;
1-[5-(4-bromophenyl)-2-furanyl]-3-(1-piperidinyl)-1-propanone hydrochloride;
1-[5-(4-chlorophenyl)-2-furanyl]-3-[1-(3-methylpiperidinyl)]-1-propanone hydrochloride;
1-[5-(4-chlorophenyl)-2-furanyl]-3-[1-(3-hydroxymethylpiperidinyl)]-1-propanone hydrochloride;
1-[5-(4-chlorophenyl)-2-furanyl]-2-(diethylamino)ethanone hydrochloride;
3-diethylamino-1-[5-(p-chlorophenyl)-2-furyl]-1-propanone hydrochloride.

As used herein, the number 2 and number 6 labeled position on the phenyl group are collectively referred to as the "ortho" or "o" position; the number 5 and number 3 labeled position are collectively referred to as the "meta" or "m" position; and the number 4 labeled position is referred to as the "para" or "p" position.

The compounds of this invention are readily prepared by methods well-known in the chemical literature. It is preferred to prepare the 5-phenyl-2-furyl ketones by reaction of a substituted 5-phenyl-2-furyl methyl ketone with the appropriate amine and paraformaldehyde in the presence of hydrochloric acid and a solvent such as butanol. Amino substituted compounds are prepared by reduction of the nitro to the amino groups in the presence of palladium-on-charcoal and a solvent such as alcohol.

COMPOSITIONS

The present invention also provides compositions for lessening the severity or frequency of epileptic seizures, comprising:

(a) a safe and effective amount of a 5-phenyl furan; and (b) a pharmaceutically-acceptable carrier.

The compositions of this invention are preferably provided in unit dosage form. As used herein, a "unit dosage form" is a composition of this invention containing an amount of a 5-phenyl furan or its pharmaceutically-acceptable salts or hydrates that is suitable for administration to a human or lower animal, in a single dose, according to good medical practice.

The unit dosage form will typically contain from 0.1 mg to 2 grams of a 5-phenyl furan. Preferably, the unit dosage form will be from 0.1 mg to 1000 mg of a 5-phenyl furan. More preferably, the unit dosage form will be from 0.1 mg to 500 mg of a 5-phenyl furan.

The compositions of this invention may be in any of a variety of forms. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the anticonvulsant activity of the 5-phenyl furan. The amount of carrier employed in conjunction with the 5-phenyl furan is sufficient to provide a practical quantity of material for administration per unit dose of the 5-phenyl furan. Techniques and compositions for making dosage forms useful in the methods of this invention are described in the following references, all incorporated by reference herein: 7 *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2nd Edition (1976).

In particular, pharmaceutically-acceptable carriers for systemic administration include water, sugars, starches, cellulose and its derivatives, malt, gelatin, talc, calcium sulfate, vegetable oils, synthetic oils, polyols, alginic acid, phosphate buffer solutions, emulsifiers, isotonic saline, pyrogen-free water, fixed oils, isopropyl myristate, benzyl benzoate, dioxolones, glycofurol, dimethylacetamide, N-($\beta$-hydroxyethyl)-lactamide, ethyl lactate, polyethylene glycols, glycerin, and 1,3 butylene glycol or a mixture of two or more of the above carriers. Pharmaceutically-acceptable carriers useful in the methods of this invention are described in *Journal of Pharmaceutical Sciences*, p. 917 (October, 1963), which is incorporated herein by reference. Preferred carriers for parenteral administration include aqueous and nonaqueous vehicles that contain or consist of, for example, water, propylene glycol, ethyl oleate, pyrrolidone, ethanol, or sesame oil. Preferably, the pharmaceutically-acceptable carrier, in compositions for parenteral administration, comprises at least about 90% by weight of the total composition.

METHODS OF TREATMENT

The present invention also encompasses a method of preventing epileptic seizures in a human or lower animal subject susceptible to said seizures which comprises systemically administering to said human or lower animal subject a safe and effective amount of a compound of this invention.

Typically, the dosage regimen consists of administration of a 5-phenyl furan one to four times per day. Preferably, the 5-phenyl furan will be administered two to four times per day. More preferably, the 5-phenyl furan will be administered once daily. Treatment regimens can extend for the life of the subject depending on the type of epileptic seizure to which the subject is susceptible.

The 5-phenyl furans and compositions of the instant invention are preferably administered systemically (i.e., through any method of introducing the 5-phenyl furan into the tissues of the body, e.g., intrathecal, epidural, intramuscular, transdermal, intravenous, intraperitoneal, subcutaneous, sublingual, and oral administration.)

Preferred methods of parenteral administration are through intravenous or intramuscular injections. As is known and practiced in the art, all formulations for parenteral administration must be sterile. For mammals, especially humans, (assuming an approximate body weight of 70 kg) individual doses of from about 0.1 mg to about 2 g of a 5-phenyl furan are acceptable. Individual doses of from about 0.1 mg to about 1 g are preferred.

A preferred method of systemic application of the 5-phenyl-furan is through oral administration. For mammals, especially humans, (assuming an approximate body weight of 70 kg) individual doses of from about 0.1 mg to about 2 g of a 5-phenyl-furan are acceptable. Individual doses of from about 0.1 mg to about 1 g are preferred.

A "safe and effective amount" of a 5-phenyl furan is an amount that is effective to inhibit epileptic seizures in a human or lower animal susceptible to said epileptic seizures, without undue adverse side effects (such as toxicity, irritation, or allergic response), commensurate with a reasonable benefit/risk ratio when used in the manner of this invention. This specific "safe and effective amount" will, obviously, vary with such factors as the particular type of epilepsy being treated, the physical condition of the patient, the duration of treatment, the nature of concurrent therapy (if any), the specific dosage form to be used, the carrier employed, and the dosage regimen desired for the composition. The most preferred dosing regimen is once or twice per day and the most preferred unit dosage form is 0.1 mg to 500 mg.

As used herein, "epileptic seizures" refer to changes in behavior or activity caused by an excessive electrical discharge in the brain cells. A susceptibility to excessive electrical discharge in the brain cells can be due to genetic inheritance, exposure to chemical toxins, disease or accident. The varieties of seizures are almost infinite because any area of the brain can be affected by the abnormal electrical discharge.

Epilepsy is not a disease in and of itself, but rather it is a collective designation for a group of chronic central nervous system disorders that are characterized by the occurrence of sudden and transitory episodes, called seizures. A person with epilepsy has recurrent seizures. Any disease, toxin or accident that affects the central nervous system can cause a seizure. Information on epilepsy can be found in *Epilepsy*, by Allen H. Middleton et al. (1981) incorporated herein by reference.

The International Classification of Epileptic Seizures classifies seizures into those that have a partial or focal onset in one area of the brain and those that have a generalized onset. There are two primary types of partial seizures: those with elementary symptomatology and those with complex symptomatology. Partial seizures with elementary symptomatology are caused by an abnormal electrical discharge that starts in one certain area of the brain; the clinical manifestations brought about by this discharge depend upon the specific area of the brain involved. For example, if the seizure involves the motor cortex, the clinical change may be a single jerk or multiple jerks of the arm or leg. Partial seizures with elementary symptomatology generally do not spread to areas of the brain involved with consciousness.

Another subcategory of focal-onset seizures is partial seizures with complex symptomatology (often called "partial complex"). A partial complex seizure is one in which abnormal discharges usually occur in both temporal lobes. Since the temporal lobes govern memory and alertness, the person experiences an impairment of consciousness.

A further subcategory is "partial seizures secondarily generalized." A seizure discharge can start in one focal area of the brain and if it spreads out to the rest of the brain the person can have a secondarily generalized tonic-clonic (grand mal) seizure. This is akin to a chain reaction wherein the abnormal discharge that begins in a few brain cells causes more and more brain cells to have abnormal discharges until the whole brain is involved.

The second major class of seizures is "generalized onset seizures." These begin without a focal onset and affect both sides of the body. In this category are found the two classic types of epilepsy: absence seizures (also referred to as petit mal seizures), and generalized tonic-clonic seizures (also referred to as grand mal seizures). In the absence seizure, the patient stares ahead for a brief period (5 to 15 seconds). After the episode, the person will probably resume what he was doing and may not be aware of the brief interruption. The patient undergoing a generalized tonic-clonic seizure usually stiffens for 30 to 60 seconds and then jerks for a similar period; or the stiffening and jerking may alternate irregularly. Tonic refers to a stiffening of the body and clonic refers to a jerking of the body. The name "generalized tonic-clonic" is derived from the lack of focal onset of the seizure and the stiffening and jerking motions during the seizure. The patient undergoing this type of seizure will also lose consciousness and fall.

The following non-limiting examples illustrate the compounds, compositions and uses of the present invention.

EXAMPLE I

3-Dimethylamino-1-[5-(4-chlorophenyl)-2-furanyl]-1-propanone Hydrochloride

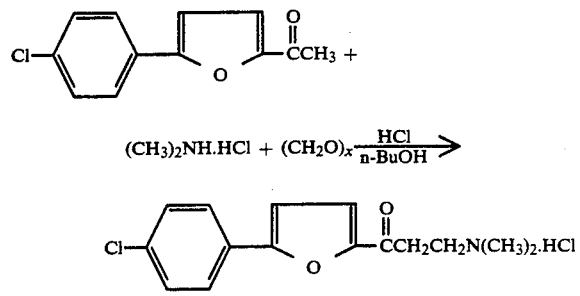

A solution of 22 g. (0.10 mole) of 5-(p-chlorophenyl)-2-furyl methyl ketone, 16 g. (0.20 mole) of dimethylamine hydrochloride, 6 g (0.20 mole) of paraformaldehyde, 100 ml. of n-butanol, and 1 ml. of concentrated HCl is heated under reflux for 2 hr. Solvent is removed on a rotary evaporator and the yellow, residual solid is partitioned between ether and water. The layers are separated and the water layer is washed with ether. The water layer is made basic with 1 N NaOH solution and is extracted twice with ether. The ethereal layers are dried over $MgSO_4$ and are concentrated on a rotary evaporator to give a residual semi-solid. The solid is dissolved in 350 ml. of isopropanol and is treated with ethereal HCl. The solid which is deposited is collected by filtration and is dried in a 60° oven to give 13 g (42%) of product.

Fifty milligrams of the above compound is administered to a human or lower animal subject susceptible to secondarily generalized tonic clonic seizures to decrease the frequency and severity of these seizures.

EXAMPLE II

1-[5-(2-Nitrophenyl)-2-furanyl]-3-(1-piperidinyl)-1-propanone Hydrochloride

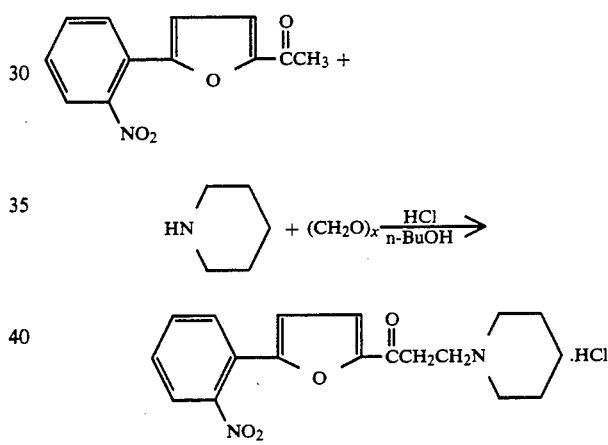

Concentrated HCl (16 ml.) is added to a stirred solution of 17 g. (0.20 mole) of piperidine in 100 ml. of n-butanol. To this solution is added 23 g. (0.10 mole) of 5-(o-nitrophenyl)-2-furyl methyl ketone and 6.0 g. (0.20 mole) of paraformaldehyde. The solution is heated under reflux for 3 hr. and the solvent is removed on a rotary evaporator. The residual semi-solid is partitioned between ether and water, the layers are separated, and the ether layer is dried over $MgSO_4$. The solvent is removed on a rotary evaporator to give a residual oil. The oil is dissolved in anhydrous ether and is treated with ethereal HCl. The solid is collected by filtration and is dissolved in 300 ml. of $CH_3CN$. The solution is concentrated and cooled in ice to give solid which is collected by filtration. Recrystallization from $CH_3CN$ and then recrystallization with absolute ethanol-anhydrous ether mixture gives 6.5 g. (28%) of product, m.p. 160°–162°.

One hundred milligrams of the above compound is administered to a human susceptible to partial complex seizures to decrease the frequency and severity of the seizures.

EXAMPLE III

3-[5-(4-Chlorophenyl)-2-furanyl]-3-oxopropanamide

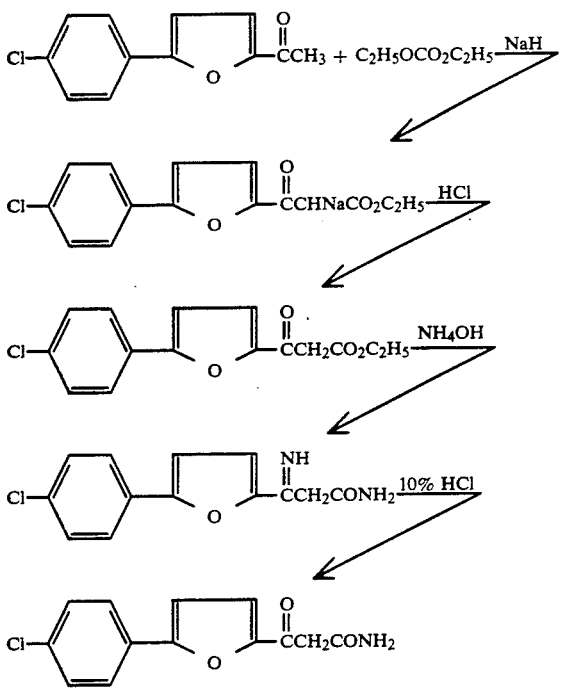

To a stirring solution of 2000 ml. of diethyl carbonate in an ice bath is added portionwise 78 g (1.94 mole) of NaH. While maintaining ice bath temperature, 213 g (0.97 mole) of 5-(p-chlorophenyl)-2-furyl methyl ketone is added portionwise. The bath is removed and the reaction is stirred at ambient temperature for one hour and then refluxed for 4 hrs. An additional 1000 ml. of diethyl carbonate is added to aid in stirring. The mixture is cooled and 130 ml. of ethanol is added dropwise. The solid is filtered, is washed with hexane and is air-dried to yield 225 g. (74%) of ethyl 3-[5-(4-chlorophenyl)-2-furanyl]-3-oxopropanate.

A 50 g. (0.16 mole) sample of ethyl 3-[5-(4-chlorophenyl)-2-furanyl]-3-oxopropanate Na salt is suspended in a mixture of 500 ml. of ether and 500 ml. of H₂O. The resulting mixture is acidified with concentrated hydrochloric acid. The ether layer is then separated, dried over MgSO₄ and concentrated on a rotary evaporator to yield a residual oil. This oil is extracted with refluxing hexane and the hexane upon cooling yields 12.5 g (27%) of product. An analytical sample is prepared by recrystallizing a sample from hexane and drying in the vacuum pistol at room temperature, m.p. 46°–47°.

A pressure vessel charged with 2 g. (0.0068 mole) of ethyl 3-[5-(4-chlorophenyl)-2-furonyl]-3-oxopropanate and 50 ml. of concentrated NH₄OH is heated in a boiling water bath for 6¼ hours. The resulting mixture is allowed to stand in the pressure vessel at room temperature for 18 hours. The solid is filtered, and then recrystallized with activated charcoal from ethyl acetate and dried in the vacuum pistol at room temperature to yield 0.5 g (28%), m.p. 212°–214°.

A mixture of 1.7 g (0.0065 mole) of 3-[5-(4-chlorophenyl)-2-furanyl]-3-iminopropanamide and 20 ml. of 10% hydrochloric acid is warmed on a steam bath with dissolution. A solid forms after 15 minutes of heating. This solid is filtered, recrystallized with activated charcoal from nitromethane, and dried for 4 days in the vacuum pistol at the temperature of boiling water to yield 1.0 g (59%) of product, m.p. 180°–181°.

Fifty milligrams of the above compound is administered to a human susceptible to partial seizures with elementary symptomatology to decrease the frequency and severity of the seizures.

EXAMPLE IV

A human subject with a history of complex partial seizures is given 25 mg of 3-dimethylamino-1-(5-phenyl-2-furanyl)-1-propanone hydrochloride tetartohydrate. The administration of 3-dimethylamino-1-(5-phenyl-2-furanyl)-1-propanone hydrochloride tetartohydrate decreases the frequency and severity of these seizures. This therapy continues on a chronic basis. In the above example, 3-dimethylamino-1-5-(4-methoxyphenyl)-2-furanyl]-1-propanone hydrochloride; and 1-[5-(4-chlorophenyl)-2-furanyl]-3-[1-(4-methylpiperazinyl)]-1-propanone dihydrochloride hemihydrate; are substituted for 3-dimethylamino-1-(5-phenyl-2-furanyl)-1-propanone hydrochloride tetartohydrate with substantially similar results.

EXAMPLE V

A human subject suffering from generalized tonic-clonic seizures is given 50 mg of 1-[5-(4-chlorophenyl)-2-furanyl]-3-[1-(4-methylpiperazinyl)]-1-propanone dihydrochloride hemihydrate twice a day. Administration of the above compound inhibits these seizures completely. This therapy continues on a chronic basis.

EXAMPLE VI

A human subject who is admitted to a hospital emergency room with a seizure of unknown origin manifested by uncontrolled arm and leg movements, is administered 50 mg of 3-dimethylamino-1-[5-(4-chlorophenyl)-2-furanyl]-1-propanone hydrochloride intravenously in a suitable solution for intravenous injection. This causes the seizure to subside within a few minutes of injection. This therapy is administered only as an emergency measure to a human subject presently experiencing a seizure whose origin is not known.

What is claimed is:

1. A compound of the formula:

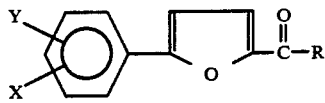

wherein
(a) X is halo or nil; and Y is a substituent selected from the group consisting of unsubstituted or halogen-substituted methyl, halo, nitro, amino, and methoxy; and
(b) R is $R^1C(O)OH$, $R^1C(O)N(R^2)_2$, or $R^1N(R^2)_2$; where
 $R^1$ is $C_1$–$C_3$ alkylene which is unsubstituted or substituted with $C_1$–$C_2$ alkyl; and
 each $R^2$ is, independently, hydrogen or lower alkyl; or both $R^2$ groups are connected to form a saturated 5- or 6-membered heterocycle containing 1 or 2 heteroatoms, wherein one of which is nitrogen and the other is selected from oxygen and nitrogen and said heterocycle is unsubstituted or substituted with lower alkyl or hydroxy-substituted lower alkyl;
or a pharmaceutically-acceptable salt thereof.

2. A compound of the formula:

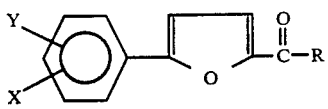

wherein
(a) X is halo or nil; and Y is a substituent selected from the group consisting of unsubstituted or halogen-substituted methyl, halo, nitro, amino, and methoxy; and
(b) R is or $R^1N(R^2)_2$ where $R^1$ is $C_1-C_3$ alkylene which is unsubstituted or substituted with $C_1-C_2$ alkyl; and each $R^2$ is, independently, hydrogen or lower alkyl; or both $R^2$ groups are connected to form a saturated 6-membered heterocycle containing 1 or 2 heteroatoms, wherein one of which is nitrogen and the other is selected from oxygen and nitrogen and said heterocycle is substituted with lower alkyl or hydroxy-substituted lower alkyl;
or a pharmaceutically-acceptable salt thereof.

3. A compound of the formula:

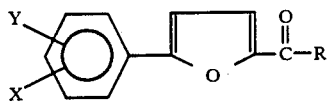

wherein
(a) X is halo or nil; and Y is a substituent selected from the group consisting of unsubstituted or halogen-substituted methyl, halo, nitro, amino, and methoxy; and
(b) R is $R^1N(R^2)_2$ where $R^1$ is $C_1-C_3$ alkylene which is unsubstituted or substituted with $C_1-C_2$ alkyl; and each $R^2$ is, independently, hydrogen or lower alkyl; or both $R^2$ groups are connected to form a saturated 5- membered heterocycle containing 1 or 2 heteroatoms, wherein one of which is nitrogen and the other is selected from oxygen and nitrogen and said heterocycle is unsubstituted or substituted with lower alkyl or hydroxy-substituted lower alkyl;
or a pharmaceutically-acceptable salt thereof.

4. A compound according to claim 1 wherein X is nil.

5. A compound according to claim 1 wherein X is halo.

6. A compound according to claim 1 wherein Y is halosubstituted methyl.

7. A compound according to claim 1 wherein Y is trifluoromethyl.

8. A compound according to claim 1 wherein Y is selected from the group consisting of: para- and meta-fluoro, para- and meta-chloro, para- and meta-trifluoromethyl, meta-nitro, para- and meta-bromo, para- and meta-methoxy, and para-methyl.

9. A composition comprising a safe and effective amount of a 5-phenyl furan according to claim 1 and a pharmaceutically-acceptable carrier.

10. A composition comprising a safe and effective amount of a 5-phenyl-furan according to claim 2 and a pharmaceutically-acceptable carrier.

11. A composition comprising a safe and effective amount of a 5-phenyl-furan according to claim 3 and a pharmaceutically-acceptable carrier.

12. A method of preventing epileptic seizures in a human or lower animal subject susceptible to said seizures, comprising systemically administering to said subject a safe and effective amount of a compound of the formula:

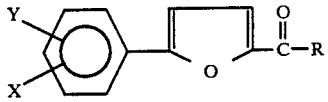

wherein
(a) X is halo or nil; and Y is a substituent selected from the group consisting of unsubstituted or halogen-substituted methyl, halo, nitro, amino, and methoxy; and
(b) R is $R^1C(O)OH$, $R^1C(O)N(R^2)_2$, or $R^1N(R^2)_2$; where
$R^1$ is $C_1-C_3$ alkylene which is unsubstituted or substituted with $C_1-C_2$ alkyl; and
each $R^2$ is, independently, hydrogen or lower alkyl;
or both $R^2$ groups are connected to form a saturated 5- or 6-membered heterocycle containing 1 or 2 heteroatoms, wherein one of which is nitrogen and the other is selected from oxygen and nitrogen and said heterocycle is unsubstituted or substituted with lower alkyl or hydroxy-substituted lower alkyl; or a pharmaceutically-acceptable salt thereof.

13. A method of preventing epileptic seizures in a human or lower animal subject susceptible to said seizures, according to claim 12 wherein X is nil.

14. A method of preventing epileptic seizures in a human or lower animal subject susceptible to said seizures, according to claim 12 wherein X is halo.

15. A method of preventing epileptic seizures in a human or lower animal subject susceptible to said seizures, according to claim 12 wherein Y is halosubstituted methyl.

16. A method of preventing epileptic seizures in a human or lower animal subject susceptible to said seizures, according to claim 15 wherein Y is trifluoromethyl.

17. A method of preventing epileptic seizures in a human or lower animal subject susceptible to said seizures, according to claim 12 wherein R is $R^1C(O)OH$ or $R^1C(O)N(R^2)_2$.

18. A method of preventing epileptic seizures in a human or lower animal subject susceptible to said seizures, according to claim 12 wherein R is $R^1C(O)N(R^2)_2$, or $R^1N(R^2)_2$; where both $R^2$ groups are connected to form a saturated 5- or 6-membered heterocycle containing 1 or 2 heteroatoms selected from oxygen and nitrogen and said heterocycle is unsubstituted or substituted with lower alkyl or hydroxy-substituted lower alkyl.

19. A method of preventing epileptic seizures in a human or lower animal subject susceptible to said seizures, according to claim 12 wherein X is nil, R is 3-diethylamino-2,2-dimethylpropyl and Y is selected from the group consisting of: para- and meta-fluoro, para and meta-chloro, para- and meta-trifluoromethyl, meta-nitro, para- and meta-bromo, para- and meta-methoxy, para-methyl, para-amino and orthochloro.

20. A method of preventing epileptic seizures in a human or lower animal subject susceptible to said seizures according to claim 14 wherein R is 3-diethylamino-2,2-dimethylpropyl and X and Y are the same substituent selected from the group consisting of chloro and fluoro.

21. A method of preventing epileptic seizures in a human or lower animal subject susceptible to said seizures according to claim 15 wherein Y is selected from the group consisting of: para- and meta-fluoro, para- and meta-chloro, para- and meta-trifluoromethyl, meta-nitro, para- and meta-bromo, para- and meta-methoxy, and para-methyl.

* * * * *

UNITED STATES PATENT AND TRADEMARK OFFICE
CERTIFICATE OF CORRECTION

PATENT NO. : 5,091,426
DATED : February 25, 1992
INVENTOR(S) : STANFORD S. PELOSI, JR.

It is certified that error appears in the above-identified patent and that said Letters Patent is hereby corrected as shown below:

Col 10, line 59, R should be:

"R is $R^1C(O)N(R^2)_2$".

Signed and Sealed this

Tenth Day of August, 1993

Attest:

MICHAEL K. KIRK

*Attesting Officer*   *Acting Commissioner of Patents and Trademarks*